United States Patent [19]

Bradbury et al.

[11] Patent Number: 5,281,613
[45] Date of Patent: Jan. 25, 1994

[54] HETEROCYCLIC COMPOUNDS

[75] Inventors: Robert H. Bradbury, Wilmslow; Andrew P. Thomas, Congleton, both of England

[73] Assignee: Imperial Chemical Industries PLC, London, England

[21] Appl. No.: 904,225

[22] Filed: Jun. 25, 1992

[30] Foreign Application Priority Data

Jun. 25, 1991 [GB] United Kingdom ............... 9113626

[51] Int. Cl.$^5$ .................. A61K 31/435; C07D 405/06
[52] U.S. Cl. .................... 514/300; 546/113; 546/122; 546/123; 546/118; 546/153; 546/167; 546/176; 546/156; 546/180; 546/269
[58] Field of Search ................ 546/113, 122, 123; 514/300

[56] References Cited

U.S. PATENT DOCUMENTS

| 4,920,131 | 4/1990 | Huang et al. | 546/156 |
| 5,028,615 | 6/1991 | Huang et al. | 514/314 |
| 5,126,344 | 6/1992 | Roberts et al. | 514/248 |
| 5,130,318 | 7/1992 | Roberts et al. | 514/299 |

FOREIGN PATENT DOCUMENTS

| 0315399 | 5/1989 | European Pat. Off. |
| 0326328 | 8/1989 | European Pat. Off. |
| 0326330 | 8/1989 | European Pat. Off. |
| 0348155 | 12/1989 | European Pat. Off. |
| 0400974 | 12/1990 | European Pat. Off. |
| 0411766 | 2/1991 | European Pat. Off. |
| 0412848 | 2/1991 | European Pat. Off. |
| 0429257 | 5/1991 | European Pat. Off. |
| 0430709 | 6/1991 | European Pat. Off. |
| 0434249 | 6/1991 | European Pat. Off. |
| 0445811 | 9/1991 | European Pat. Off. |
| 0475206 | 3/1992 | European Pat. Off. |
| 0487745 | 6/1992 | European Pat. Off. |
| 0488532 | 6/1992 | European Pat. Off. |
| 0399731 | 11/1992 | European Pat. Off. |
| WO91/07404 | 5/1991 | PCT Int'l Appl. |

OTHER PUBLICATIONS

G. R. Proctor, et al., "Azabenzocycloheptenones. Part XIV. Cyclisation of Amino-acid Derivatives to Tetrahydro-1-benzazepin-5-ones and Tetrahydroquiolin-4-ones" *J. Chem. Soc., Perkin Trans. I* (1972), 1803-8.

R. D. Youssefyeh, et al. (principal author Huang) *J. Med. Chem.* (1990), 33, 1186–1194; *Chem. Abstr.* (1990), *112, 17, abstract 131,890u.*

F-C. Huang *J. Med. Chem.* (1990), 33, 1194–1200.

*Primary Examiner*—C. Warren Ivy
*Assistant Examiner*—James H. Turnipseed

[57] ABSTRACT

The invention concerns pharmaceutically useful compounds of the formula I, in which Q, X, $G^1$, Z and Ra have the various meanings defined herein, and their non-toxic salts, and pharmaceutical compositions containing them. The novel compounds are of value in treating conditions such as hypertension and congestive heart failure. The invention further concerns processes for the manufacture of the novel compounds and the use of the compounds in medical treatment.

9 Claims, No Drawings

HETEROCYCLIC COMPOUNDS

This invention concerns novel heterocyclic compounds and, more particularly, novel heterocyclic compounds which possess pharmacologically useful properties in antagonising at least in part one or more of the actions of the substances known as angiotensins, and in particular of that known as angiotensin II (hereinafter referred to as "AII"). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the afore-mentioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) on angiotensin I, itself produced by the action of the enzyme renin on the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

In our published co-pending European Patent Applications, Publication Nos. 399731, 412848, 454831 and 453210 there are respectively disclosed certain imidazopyridine, quinoline, naphthyridine and pyridine derivatives which have AII antagonist activity.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided a heterocyclic compound of the formula I (set out hereinafter, together with the other chemical formulae identified by Roman numerals) wherein Q is selected from a group of the partial structural formula IIa, IIb, IIc or IId in which ring B of formula IIa completes a benzene or pyridine ring;

$R^1$ and $T^1$ are independently selected from (1–8C)alkyl, (3–8C)cycloalkyl, (3–8C)cycloalkyl-(1–4C)alkyl, phenyl, phenyl(1–4C)alkyl or substituted (1–4C)alkyl, the latter containing one or more fluoro substituents or bearing an (1–4C)alkoxy substituent;

$R^2$ and $T^2$ are independently selected from hydrogen, (1–8C)alkyl, (3–8C)cycloalkyl, (3–8C)cycloalkyl-(1–4C)alkyl, carboxy, (1–4C)alkoxycarbonyl, (3–6C)alkenyloxycarbonyl, cyano, nitro, phenyl or phenyl(1–4C)alkyl;

$R^3$ and $R^4$ are optional substituents on ring B independently selected from (1–4C)alkyl, (1–4C)alkoxy, halogeno, trifluoromethyl, cyano, nitro, fluoro(1–4C)alkoxy, hydroxy or hydroxy(1–4C)alkyl;

$T^3$ is selected from halogeno, (1–4C)alkoxy, amino, alkylamino and dialkylamino of up to 6 carbon atoms and any of the values defined for $T^1$;

$T^4$ is selected from hydrogen, (1–4C)alkyl, (1–4C)alkoxy, (1–4C)alkyl containing one or more fluoro substituents, carboxy, (1–4C)alkoxycarbonyl, (3–6C)alkenyloxycarbonyl, halogeno, cyano, nitro, carbamoyl, (1–4C)alkanoyl, N-alkylcarbamoyl and di-(N-alkyl)carbamoyl of up to 7 carbon atoms, amino, alkylamino and dialkylamino of up to 6 carbon atoms, and a group of the formula $-A^1.B^1$ wherein $A^1$ is (1–6C)alkylene, a carbonyl group or a direct bond and $B^1$ is (1) an unsubstituted phenyl or phenyl bearing one or two substituents independently selected from (1–4C)alkyl, (1–4C)alkoxy, halogeno, cyano, trifluoromethyl, nitro, hydroxy, carboxy, (1–4C)alkanoylamino, (1–4C)alkanoyl, fluoro(1–4C)alkoxy, hydroxy(1–4C)alkyl, (1–4C)alkyl, carbamoyl, N-alkyl or di-(N-alkyl)carbamoyl of up to 7 carbon atoms, sulphamoyl, N-alkyl or di-(N-alkyl)sulphamoyl of up to 6 carbon atoms, (1–4C)alkoxycarbonyl, (1–4C)alkanesulphonamido, (1–4C)alkyl.-$S(O)_n$—[in which n is zero, 1 or 2] and 1H-tetrazol-5-yl; or $B^1$ is (2) a 5 or 6-membered saturated or unsaturated heterocyclic ring optionally bearing a (1–4C)alkyl group and containing a single heteroatom selected from oxygen, sulphur and nitrogen or containing two heteroatoms one of which is nitrogen and the other is oxygen, sulphur or nitrogen;

or $T^3$ and $T^4$ together form an (3–6C)alkenylene group, an (3–6C)alkylene group or an (3–6C)alkylene group in which a methylene is replaced by carbonyl, provided that when $T^3$ and $T^4$ together form one of said latter three groups then $T^2$ is additionally selected from any of the previous values defined for $T^4$; Y is oxygen or a group of the formula —NRb— wherein Rb is hydrogen, (1–4C)alkyl, (1–4C)alkanoyl or benzoyl; linking group A of formula IIc is selected from —CH=CH—, —CH=CH—CO—, —CO—CH=CH—, —CO—CH$_2$—CH$_2$—, —CH$_2$—CH$_2$—CO, —CH$_2$-CO and —CO—CH$_2$—; $E^1$ is hydrogen, (1–8C)alkyl or trifluoromethyl; $E^2$ is hydrogen, (1–8C)alkyl, halogeno, (1–4C)alkoxy, trifluoromethyl, carboxy, (1–4C)alkoxycarbonyl, (3–6C)alkenyloxycarbonyl, cyano, nitro, (1–4C)alkanoyl, (1–4C)alkyl.S(O)$_m$— [in which m is zero, 1 or 2 ] or phenylsulphonyl; $E^3$ is hydrogen, (1–8C)alkyl, (1–4C)alkoxy, halogeno or trifluoromethyl; $E^4$ and $E^5$ are optional substituents on linking group A independently selected from (1–4C)alkyl, substituted (1–4C)alkyl containing one or more fluoro substituents, phenyl, pyridyl, alkoxy, halogeno, cyano, nitro, carboxy, (1–4C)alkoxycarbonyl, (3–6C)alkenyloxycarbonyl, carbamoyl, N-alkylcarbamoyl and di-(N-alkyl)carbamoyl of up to 7 carbon atoms, (1–4C)alkylthio, (1–4C)alkylsulphinyl, (1–4C)alkylsulphonyl, phenylthio, phenylsulphinyl, phenylsulphonyl and (1–4

C)alkanoyl; $L^1$ is (1–8C)alkyl; $L^2$ and $L^3$ are independently selected from hydrogen and (1–4C)alkyl; $G^1$ is selected from hydrogen, (1–4C)alkyl optionally bearing one or more fluoro substituents, halogeno, cyano, (1–4C)alkoxycarbonyl, (1–4C)alkanoyl, carbamoyl and N-alkylcarbamoyl and di-(N-alkyl)carbamoyl of up to 7 carbon atoms; X is oxygen, sulphur or a group of the formula -NRc wherein Rc is hydrogen or (1–4C)alkyl; Ra is selected from hydrogen, (1–4C)alkyl, (1–4C)alkoxy, halogeno, trifluoromethyl, cyano and nitro; Z is 1H-tetrazol-5-yl, carboxy or a group of the formula $CF_3SO_2NH-$; and wherein any of said phenyl moieties of $R^1$, $R^2$, $T^1$, $T^2$, $T^3$ or $E^2$ may be unsubstituted or bear one or two substituents independently selected from (1–4C)alkyl, (1–4C)alkoxy, halogeno, cyano and trifluoromethyl; or a non-toxic salt thereof.

It will appreciated that, depending on the nature of the substituents, certain of the formula I compounds may possess one or more chiral centres and may be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$, $R^2$, $T^1$ or $T^2$ where appropriate, include, by way of example, for alkyl: methyl, ethyl, propyl, butyl, isobutyl, sec-butyl, pentyl and hexyl; for cycloalkyl: cyclopropyl, cyclopentyl and cyclohexyl; for alkyl containing one or more fluoro substituents: fluoromethyl, trifluoromethyl, 2,2,2-trifluoroethyl and pentafluoroethyl; for alkyl bearing an (1–4C)alkoxy substituent: 2-methoxyethyl and 2-ethoxyethyl; for cycloalkyl-alkyl: cyclopropylmethyl, cyclopentylmethyl, cyclohexylmethyl and 2-cyclopentylethyl; for phenylalkyl: benzyl, 1-phenylethyl and 2-phenylethyl; for alkoxycarbonyl: methoxycarbonyl, ethoxycarbonyl and propoxycarbonyl; and for alkenyloxycarbonyl: allyloxycarbonyl, 2-methyl-2-propenyloxycarbonyl and 3-methyl-3-butenyloxycarbonyl.

A particular value for $T^3$, $T^4$, or for $T^2$ when it is selected from a value for $T^4$, where appropriate, includes, by way of example, for alkyl: methyl, ethyl and propyl; for alkoxycarbonyl: methoxycarbonyl, ethoxycarbonyl and propoxycarbonyl; for alkenyloxycarbonyl: allyloxycarbonyl, 2-methyl-2-propenyloxycarbonyl and 3-methyl-3-butenyloxycarbonyl; for halogeno: fluoro, chloro, bromo and iodo; for alkoxy: methoxy, ethoxy and propoxy; for alkyl containing one or more fluoro substituents: fluoromethyl, trifluoromethyl, 2,2,2-trifluoroethyl and pentafluoroethyl; for alkanoyl: formyl, acetyl and butyryl; for N-alkylcarbamoyl: N-methyl and N-ethylcarbamoyl; for di(N-alkyl)carbamoyl: N,N-dimethylcarbamoyl and N,N-diethylcarbamoyl; for alkylamino: methylamino, ethylamino and butylamino; and for dialkylamino: dimethylamino, diethylamino and dipropylamino.

A particular value for $A^1$ when it is alkylene is, for example, methylene, ethylene or propylene.

Particular values for $R^3$, $R^4$ or an optional substituent on $B^1$ when it is phenyl bearing one or two substituents, where appropriate, include, by way of example, for alkyl: methyl and ethyl; for alkoxy: methoxy and ethoxy; for halogeno: chloro, bromo and iodo; for alkanoylamino: formamido, acetamido and propanamido; for alkanoyl: formyl, acetyl and butyryl; for fluoroalkoxy: trifluoromethoxy, 2-fluoroethoxy, 2,2,2-trifluoroethoxy and 3,3,3-trifluoropropoxy; for hydroxyalkyl: hydroxymethyl, 1-hydroxyethyl and 2-hydroxyethyl; for alkoxyalkyl: 2-methoxyethyl and 2-ethoxyethyl; for N-alkylcarbamoyl: N-methyl and N-ethylcarbamoyl; for di(N-alkyl)carbamoyl: N,N-dimethylcarbamoyl and N,N-diethylcarbamoyl; for N-alkylsulphamoyl: N-methyl and Nethylsulphamoyl; for di(N-alkylsulphamoyl: N,N-dimethylsulphamoyl and N,N-diethylsulphamoyl; for alkoxycarbonyl: methoxycarbonyl, ethoxycarbonyl and propoxycarbonyl; for alkanesulphonamido: metanesulphonamido and ethanesulphonamido; for alkylthio: methylthio and ethylthio; for alkylsulphinyl; methylsulphinyl and ethylsulphinyl; and for alkylsulphonyl: methylsulphonyl and ethylsulphonyl.

A particular value for $B^1$ when it is a 5 or 6-membered saturated or unsaturated heterocyclic ring containing a single hetero atom selected from oxygen, sulphur or nitrogen includes, for example, a thienyl, furyl, pyrrolyl, pyrrolidinyl, pyridyl and piperidyl ring.

A particular value for $B^1$ when it is a 5 or 6-membered saturated or unsaturated heterocyclic ring containing two heteroatoms one of which is nitrogen and the other is oxygen, sulphur or nitrogen includes, for example, an imidazolyl, imidazolidinyl, pyrazolyl, pyrazolinyl, thiazolyl, thiazolinyl, oxazolyl, oxazolidinyl, pyrimidinyl, pyrazinyl, pyridazinyl, piperazinyl, morpholinyl and thiomorpholinyl ring.

A particular value for an alkyl group which may be present on $B^1$ when it is a saturated or unsaturated heterocyclic ring is, for example, methyl or ethyl.

A particular value for $T^3$ and $T^4$ when together they form (3–6C)alkylene is, for example, trimethylene, tetramethylene or pentamethylene; when together they form (3–6C)alkenylene is, for example, 1-propenylene, 2-propenylene, 1-butenylene, 2-butenylene or 3-butenylene; and when together they form (3–6C)alkylene wherein one of the methylene groups is replaced by a carbonyl group is, for example, 1-oxopropylidene, 3-oxopropylidene, 1-oxobutylidene or 4-oxobutylidene.

A particular value for Rb when it is alkyl is, for example, methyl or ethyl; and when it is alkanoyl is, for example, formyl, acetyl or propanoyl.

A particular value for $E^1$, $E^2$, $E^3$ or $L^1$ when it is alkyl is, for example, methyl, ethyl, propyl, butyl, isobutyl, sec-butyl, pentyl or hexyl.

A particular value for $E^2$ or $E^3$ when it is halogeno is, for example, fluoro, chloro, bromo or iodo; and when it is alkoxy is, for example, methoxy, ethoxy or propoxy.

A particular value for $E^2$ when it is alkoxycarbonyl is, for example, methoxycarbonyl, ethoxycarbonyl or propoxycarbonyl; when it is alkenyloxycarbonyl is, for example, allyloxycarbonyl, 2-methyl-2-propenyloxycarbonyl or 3-methyl-3-butenyloxycarbonyl; when it is alkanoyl is, for example, formyl, acetyl or butyryl; when it is alkylthio is, for example, methylthio or ethylthio; when it is alkylsulphinyl is, for example, methylsulphinyl or ethylsulphinyl; and when it is alkylsulphonyl is, for example, methylsulphonyl or ethylsulphonyl.

Particular values for $E^4$ or $E^5$ include, by way of example, for alkyl: methyl and ethyl; for alkyl containing one or more fluoro substituents: fluoromethyl, trifluoromethyl, 2,2,2-trifluoroethyl and pentafluoroethyl; for alkoxy: methoxy and ethoxy; for halogeno: chloro, bromo and iodo; for alkoxycarbonyl: methoxycarbonyl, ethoxycarbonyl and propoxycarbonyl; for alkenyloxycarbonyl: allyloxycarbonyl, 2-methyl-2-propenyloxycarbonyl and 3-methyl-3-butenyloxycarbonyl; and for alkanoyl: formyl, acetyl or butyryl; for N-alkylcarbamoyl: N-methylcarbamoyl and N-ethylcarbamoyl; for di-(N-alkyl)carbamoyl: N,N-dimethylcarbamoyl and N,N-diethylcarbamoyl; for alkylthio: methylthio and ethylthio; for alkylsulphinyl: methylsulphinyl and ethylsulphinyl; and for alkylsulphonyl: methylsulphonyl and ethylsulphonyl.

A particular value for $L^2$, $L^3$ or Rc when it is alkyl is, for example, methyl or ethyl.

A particular value for $G^1$ includes, by way of example, for alkyl: methyl, ethyl and propyl; for alkyl bearing one or more fluoro substituents: fluoromethyl, trifluoromethyl, 2,2,2-trifluoroethyl or pentafluoroethyl; for halogeno: chloro, bromo and iodo; for alkoxycarbonyl: methoxycarbonyl and ethoxycarbonyl; for alkanoyl: formyl, acetyl or butyryl; for alkylcarbamoyl: N-methylcarbamoyl and N-ethylcarbamoyl; and for dialkylcarbamoyl: N,N-dimethylcarbamoyl or N,N-diethylcarbamoyl.

A particular value for Ra or for an optional substituent which may be present on a phenyl moiety of $R^1$, $R^2$, $T^1$, $T^2$, $T^3$ or $E^2$ include, by way of example, for alkyl: methyl and ethyl; for alkoxy: methoxy and ethoxy; and for halogeno: chloro, bromo and iodo.

A value for $R^1$, $T^1$ or $T^3$ of particular interest is, for example, methyl, ethyl or propyl.

A value for $R^2$ of particular interest is, for example, hydrogen.

A value for $T^2$ of particular interest is, for example, hydrogen, alkoxycarbonyl or, when $T^3$ and $T^4$ form alkylene is, for example, halogeno.

A value for $T^4$ of particular interest is, for example, alkoxycarbonyl or halogeno.

A value of particular interest for $T^3$ and $T^4$ when together they form alkylene is, for example, trimethylene or tetramethylene.

A value for Y of particular interest is, for example, oxygen or a group of the formula —NRb— in which Rb is hydrogen.

A value for linking group A of formula IIc of particular interest is, for example, an optionally substituted group of the formula —CH=CH—, —CH=CH—CO— or —CH$_2$—CH$_2$—CO—.

A value of particular interest for $E^1$ is, for example, methyl, ethyl or propyl; for $E^2$ is, for example, hydrogen; for $E^3$ is, for example, methyl, ethyl or halogeno; for $E^4$ or $E^5$ is, for example, hydrogen, alkyl (such as methyl or ethyl), halogeno, phenyl, pyridyl, alkoxycarbonyl, carbamoyl, N,N-dialkylcarbamoyl, cyano, hydroxy, phenylthio, or phenylsulphinyl.

A value of particular interest for $L^1$ is, for example, (1–4C)alkyl such as ethyl, propyl or butyl; and for $L^2$ and $L^3$ is, for example, methyl.

A value of particular interest for Q is, for example, 2-(1–4C)alkylquinolin-4-yloxy (such as 2-methylquinolin-4-yloxy or 2-ethylquinolin-4-yloxy), 2-(1–4C)alkyl-5,6,7,8-tetrahydroquinolin-4-yloxy (such as 2-methyl-5,6,7,8-tetrahydroquinolin-4-yloxy or 2-ethyl-5,6,7,8-tetrahydroquinolin-4-yloxy), 2,6-di-(1–4C)alkyl-3-halogenopyrid-4-ylamino (such as 2,6-dimethyl-3-chloropyrid-4-ylamino, 2,6-dimethyl-3-iodopyrid-4-ylamino, 2,6-diethyl-3-chloropyrid-4-ylamino or 2,6-diethyl-3-iodopyrid-4-ylamino), 2,6-di-(1–4C)alkyl-4-halogeno-1H-pyrrolo[3,2-c]pyrid-1-yl (such as 2,6-dimethyl-4-chloro-1H-pyrrolo[3,2-c]pyrid-1-yl), 5,7-di-(1–4C)alkyl-2-oxo-1,2-dihydro-1,6-naphthyridin-1-yl (such as 5,7-dimethyl-2-oxo-1,2-dihydro-2-oxo-1,6-naphthyridin-1-yl or 5,7-diethyl-2-oxo-1,2-dihydro-2-oxo-1,6-naphthyridin-1-yl), 5,7-di-(1–4C)alkyl-2-oxo-1,2,3,4-tetrahydro-1,6-naphthyridin-1-yl (such as 5,7-dimethyl-2-oxo-1,2,3,4-tetrahydro-1,6-naphthyridin-1-yl or 5,7-diethyl-2-oxo-1,2,3,4-tetrahydro-1,6-naphthyridin-1-yl), 2-(1–4C)alkyl-3H-imidazo[4,5-b]pyrid-3-yl (such as 2-butyl-3H-imidazo[4,5-b]pyrid-3-yl) or 2,5,7-tri-(1–4C)alkyl-3H-imidazo[4,5-b]-pyrid-3-yl (such as 2-ethyl-5,7-dimethyl-3H-imidazo[4,5-b]pyrid-3-yl. Of these values for Q, those which are embraced by partial structural formula IIb or IIc are of special interest, especially those which are within sub-groups (c), (d) or (e) below.

A preferred value for $G^1$ is, for example, hydrogen or halogeno, especially bromo.

A preferred value for X is, for example, oxygen or a group of the formula NRc in which Rc is hydrogen, of which oxygen is particularly preferred.

A preferred value for Ra is, for example, hydrogen.

A preferred value for Z is, for example, 1H-tetrazol-5-yl.

A combination of values of special interest is, for example, when $R^1$ and $R^3$ are both alkyl; when $T^1$ and $T^3$ are both alkyl; when $T^1$ is alkyl and $T^3$ together with $T^4$ form alkylene; or when $E^4$ and $E^5$ are both hydrogen.

A particular group of compounds of the formula I which are of interest comprises compounds of the formula I as defined above but excluding those compounds wherein one or both of $E^4$ and $E^5$ is selected from phenyl, pyridyl, carbamoyl, N-alkylcarbamoyl and di-(N-alkyl)carbamoyl of up to 7 carbon atoms, (1–4C)alkylthio, (1–4C)alkylsulphinyl, (1–4C)alkylsulphonyl, phenylthio, phenylsulphinyl and phenylsulphonyl; or a non-toxic salt thereof.

Particular groups of compounds of the invention comprise those compounds of the formula I in which Q constitutes:

(1) a group of the partial structural formula IIa in which ring B, $R^1$, $R^2$, $R^3$ and $R^4$ have any of the values defined hereinbefore;

(2) a group of the partial structural formula IIb in which $T^1$, $T^2$, $T^3$, $T^4$ and Y have any of the values defined hereinbefore;

(3) a group of the partial structural formula IIc in which $E^1$, $E^2$, $E^3$, $E^4$, $E^5$ and linking group A have any of the values defined hereinbefore; and (4) a group of the partial structural formula IId in which $L^1$, $L^2$ and $L^3$ have any of the values defined hereinbefore;

and wherein in each of said groups the variables $G^1$, X, Z and Ra have any of the values defined hereinbefore; together with the non-toxic salts thereof.

Sub-groups of compounds of the invention of special interest from within the groups of compounds of particular interest (1) to (4) above comprise those compounds of the formula I in which Q constitutes:

(a) a group of the partial structural formula IIa wherein ring B together with the pyridine ring to which it is attached constitutes a quinoline ring;

(b) a group of the partial structural formula IIa wherein ring B together with the pyridine ring to which it is attached constitutes a pyrido-pyridine ring (that is a naphthyridine);

(c) a group of the partial structural formula IIb wherein Y is an oxygen atom;

(d) a group of the partial structural formula IIb wherein Y is a group of the formula —NH—;

(e) a group of the partial structural formula IIc wherein linking group A together with the nitrogen atom and pyridine ring to which it is attached constitutes a 1,6-naphthyridin-2(1H)-one or a 1,2,3,4-tetrahydronaphthyridin-2-one ring; and (f) a group of the partial structural formula IIc wherein linking group A together with the nitrogen atom and pyridine ring to which it is attached constitutes a 1H-pyrrolo[3,2-c]pyridine ring;

and wherein in each of said groups $R^1$, $R^2$, $R^3$, $R^4$, $T^1$, $T^2$, $T^3$, $T^4$, $E^1$, $E^2$, $E^3$, $E^4$ and $E^5$, where present have any of the values defined above and the variables $G^1$, X, Z and Ra have any of the values defined hereinbefore; together with the non-toxic salts thereof.

Preferred compounds of the formula I from within those contained in groups (1), (2), (3) or (4) or within sub-groups (a), (b), (c), (d), (e) or (f) above are those wherein the group Q—$CH_2$— is attached at the 5-position of the ring. Of these, those compounds in which X is oxygen or a group of the formula —NRc wherein Rc is hydrogen or (1-4C)alkyl are particularly preferred, and especially those compounds in which X is —NH— or oxygen, particularly the latter.

Compounds of the invention which are of particular interest include, for example, the specific embodiments set out hereinafter in the accompanying Examples. Of these, the compounds of formula I described in Examples 8 and 9 are of special interest and these compounds, or a non-toxic salt thereof, are provided as a further feature of the invention.

It will be appreciated that the formula I compounds can form salts with suitable acids or bases. Particularly suitable non-toxic salts for such compounds include, for example, salts with bases affording physiologically acceptable cations, for example, alkali metal (such as sodium and potassium), alkaline earth metal (such as magnesium and calcium), aluminium and ammonium salts, as well as salts with suitable organic bases, such as with ethanolamine, methylamine, diethylamine or triethylamine, as well as salts with acids forming physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise:

a) For those compounds in which Z is carboxy, a carboxylic acid derivative of the formula III, in which W is a protected carboxy group selected from (1-6C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1-4C)alkanol, such as aqueous methanol or ethanol. However, it may also be performed in a mixture of an aqueous and non-aqueous solvent such as water and toluene using a conventional quaternary ammonium phase transfer catalyst. The hydrolysis is generally performed at a temperature in the range, for example, 0°-120° C., depending on the reactivity of the group W. In general, when W is carbamoyl, temperatures in the range, for example, 40°-120° C. are required to effect the hydrolysis.

Alternatively, when W is benzyloxycarbonyl the conversion may also be performed by hydrogenolysis, for example using hydrogen at 1-3 bar in the presence of a suitable catalyst, such as palladium on charcoal or on calcium sulphate, in a suitable solvent or diluent such as a (1-4C)alkanol (typically ethanol or 2-propanol) and at a temperature in the range, for example, 0°-40° C.

Further, when W is t-butoxycarbonyl, the conversion may also be carried out by hydrolysis at a temperature in the range, for example, 0°-100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula IV in which $P^1$ is a suitable protecting group, such as trityl, benzhydryl, trialkyltin (for example trimethyltin or tributyltin) or triphenyltin, affixed to a nitrogen of the tetrazolyl moiety, is deprotected.

The reaction conditions used to carry out the deprotection necessarily depend on the nature of the group $P^1$. As an illustration, when it is trityl, benzhydryl, trialkyltin or triphenyltin, the decomposition conditions include, for example, acid catalysed hydrolysis in a mineral acid (such as aqueous hydrochloric acid), conveniently in an aqueous solvent (such as aqueous dioxan, methanol or 2-propanol). Alternatively, a trityl or benzhydryl group may be removed by hydrogenolysis, for example as described in (a) above for conversion of a benzyloxycarbonyl to a carboxy.

Compounds of the formula IV wherein $P^1$ is trialkyltin or triphenyltin may be obtained, for example, by reaction of a nitrile of the formula IX with a trialkyltin azide, such as tributyltin azide, or triphenyltin azide respectively. The reaction is conveniently carried out in a suitable solvent or diluent, such as toluene or xylene, and at a temperature in the range, for example, 50°-150° C. In a modified procedure, a formula I compound wherein Z is tetrazolyl may be obtained directly by in situ removal of the trialkyltin or triphenyltin group without prior isolation of the formula III compound, for example, by the addition of aqueous mineral acid or gaseous hydrogen chloride to the reaction mixture. Nitriles of the formula IX may be obtained, for example, by alkylation of a compound of the formula Q.H with a nitrile of the formula X wherein Hal. stands for a suitable leaving group such as chloro, bromo, iodo, methanesulphonyloxy or p-toluenesulphonyloxy, using similar conditions to those used in process (c) described hereinafter. The necessary compounds of formula X may be made by standard procedures such as those described in European Patent Applications (EPA), Publication Nos. 429257 and 430709, or by analogy therewith. Alternatively, the nitriles of the formula IX may be obtained from stepwise conversion of a compound of formula I wherein Z is a carboxy group or a compound of the formula III under standard conditions. Additionally, a nitrile of the formula IX wherein Q is a group of the partial structural formula IIb in which Y is the group —NRb— and Rb is alkanoyl or benzoyl may be obtained from the corresponding compound wherein Rb is hydrogen by acylation or benzoylation under standard conditions.

It will be appreciated that procedures (a) and (b) may be carried out with a compound of the formula III or IV respectively in which one or more functional groups of Q and X are protected with suitable protecting groups. For example, when X is an imino (—NH—) group it may be protected with a suitable nitrogen protecting group such as an acyl group (for example acetyl, trichloroacetyl or trifluoroacetyl) or an alkyloxycarbonyl group (for example tert-butyloxycarbonyl). The protecting groups may be removed either during the carrying out of procedure (a) or (b), dependent on the conditions employed, or subsequent thereto using conventional techniques. For example, a tert-butyloxycarbonyl group used to protect X when it is imino may be removed by base hydrolysis, using for example an alkali metal hydroxide (such as sodium hydroxide) in a suitable solvent (such as methanol or ethanol) and at a temperature in the range of 0° to 100° C., preferably 75° C. to ambient temperature.

c) A compound of the formula Q.H (or a tautomer thereof) is alkylated with a compound of the formula V wherein Hal. stands for a suitable leaving group such as chloro, bromo, iodo, methanesulphonyloxy or p-toluenesulphonyloxy.

The reaction is preferably carried out in the presence of a suitable base, for example, an alkali metal alkoxide such as sodium or potassium methoxide, ethoxide or tert-butoxide, an alkali metal hydride such as sodium hydride, or an alkali metal carbonate such as sodium or potassium carbonate, or an organic base such as diisopropylethylamine or 4-dimethylaminopyridine. The reaction is conveniently carried out in a suitable solvent or diluent, for example, a (1–4C)alkanol such as methanol or ethanol, an ether such as tetrahydrofuran or dioxan, or a polar solvent such as N,N-dimethylformamide or N-methylpyrrolidone and at a temperature in the range, for example, 10°–100° C. In carrying out process (c), about two molecular equivalents of a suitable base is generally required.

It will be appreciated that it may be necessary to carry out procedure (c) with a starting material of formula V and/or Q.H in which one or more functional groups present are protected with suitable protecting groups. It will also be appreciated that procedure (c) is suitable for the production of the starting materials of formula III for the reaction described in (a) above if a compound of the formula Va is used in place of a formula V compound. Similarly, using an analogous procedure, but starting with the appropriate compound of the formula VI, the starting materials of the formula IV may be obtained for procedure (b). The compounds of formula V, Va and VI may be obtained as described in EPA, Publication Nos. 429257 and 430709 or by analogy therewith.

Many of the compounds of formula Q.H (or the tautomers thereof) are already known and the remainder can be made by analogy therewith using standard procedures of organic chemistry well known in the art, for example as described in standard works of heterocyclic chemistry such as that edited by Elderfield. Certain 4-quinolones are described in EPA, Publication No. 412848 and certain 4-naphthyridones are described in International Patent Application No. PCT/GB90/01776. Certain 4-pyridones are described in *Monatshefte fur Chemie*, 1969, 100, 132; *J. Chem. Soc.* (B), 1968, 866; *Liebigs Ann. Chem.*, 1882, 1656; *Heterocycles*, 1982, 13, 239; and *J. Am. Chem. Soc.*, 1974, 96(4), 1152. Certain 4-aminopyridines may be obtained as described in *Tet. Lett.*, 1990, 3485 from intermediates obtainable as described in J. Het. Chem., 1989, 26, 1575 or European Patent No. 129408. Certain imidazo[4,4-b]pyridines are described in EPA 399731 and EPA 400974. Other compounds of the formula Q.H may be obtained as illustrated in Schemes 1 to 10, or by analogy therewith.

d) For those compounds of formula I wherein Z is a group of the formula $CF_3SO_2NH$—, a compound of the formula VII is reacted with trifluoromethanesulphonic acid anhydride.

The reaction is preferably carried out in the presence of a base, such as triethylamine, and conveniently in a suitable solvent or diluent, for example dichloromethane, and at a temperature in the range of —78° C. to ambient temperature. The compounds of the formula VII may be obtained by alkylation of a compound of formula Q.H with a compound of the formula VIII (itself obtained using analogous procedures to those described in EPA 429257 and 430709) using similar conditions to those of process (c) above, followed by reduction of the nitro group in the intermediate obtained, for example by conventional catalytic hydrogenation.

Whereafter, those compounds of formula I wherein Z is 1H-tetrazol-5-yl may be obtained by stepwise conversion of a compound of the formula I wherein Z is a carboxy group, or a compound of the formula III, into the corresponding nitrile under standard conditions, followed by reaction of the nitrile with an azide such as an alkali metal azide, preferably in the presence of an ammonium halide, and preferably in the presence of a suitable polar solvent such as N,N-dimethylformamide and at a temperature in the range, for example, 50° to 160° C.

Whereafter, when a non-toxic salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl-(1-phenylethyl)ammonium hydroxide or 1-phenylethylamine, followed by conventional separation of the diastereoisomeric mixture of salts thus obtained, for example by fractional crystallisation from a suitable solvent, for example a (1-4 C)alkanol, whereafter the optically active form of said compound of formula I may be liberated by treatment with acid using a conventional procedure, for example using an aqueous mineral acid such as dilute hydrochloric acid.

Certain of the intermediates defined herein are novel, for example the compounds of the formula III, IV, IX and X, and are provided as a further feature of the invention.

As stated above, the compounds of formula I will have beneficial pharmacological effects in warm-blooded animals (including man) in diseases and medical conditions where amelioration of the vasoconstrictor and fluid retaining properties of the reninangiotensin-aldosterone system is desirable, at least in part by antagonism of one or more of the physiological actions of AII. The compounds of the invention will thus be useful in the treatment of diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The compounds of the invention may also be useful for the treatment of ocular hypertension, glaucoma, cognitive disorders (such as Alzheimer's disease, amnesia, senile dementia and learning disorders), as well as other diseases such as renal failure, cardiac insufficiency, post-myocardial infarction, cerebrovascular disorders, anxiety, depression and certain mental illnesses such as schizophrenia.

The antagonism of one or more of the physiological actions of AII and, in particular, the antagonism of the interaction of AII with the receptors which mediate its effects on a target tissue, may be assessed using one or more of the following, routine laboratory procedures:

Test A

This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particlate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}$M are retested at lower concentrations to determine their potency. For determination of the $IC_{50}$ (concentration for 50% displacement of radiolabelled AII binding), concentrations of the test compound are ordinarily chosen to allow testing over at least four orders of magnitude centred about the predicted approximate $IC_{50}$, which latter is subsequently determined from a plot of percentage displacement against concentration of the test compound.

In general, the compounds of formula I as defined above show significant inhibition in Test A at a concentration of about 50 micromolar or much less.

Test B

This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, the compounds of formula I as defined above show significant inhibition in Test B at a final concentration of about 50 micromolar or much less.

Test C

This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific, the effect of the test compound on vasopressin-induced pressor responses may also be determined in the same preparation.

The compounds of formula I generally show specific AII-antagonist properties in Test C at a dose of about 50 mg/kg body weight or much less, without any overt toxicological or other untoward pharmacological effect.

Test D

This in vivo test involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula I will show AII-antagonist properties in Test D as demonstrated by a significant reduction in blood pressure at a dose of about 50 mg/kg body weight or much less, without any overt toxicological or other untoward pharmacological effect.

By way of illustration of the angiotensin II inhibitory properties of compounds of the formula I, the compound of Example 8 gave the following results in tests A and C described above:

In test A: an $IC_{50}$ of $3 \times 10^{-8}$M;

In test C: an $ED_{50}$ of 8.2 mg/kg (i.v. administration).

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a salt thereof, as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I may also be advantageously administered for therapeutic or prophylactic purposes together with another pharmacological agent known in the general art to be of value in treating one or more of the diseases or medical conditions referred to hereinabove, such as a beta-adrenergic blocker (for example atenolol), a calcium channel blocker (for example nifedipine), an angiotensin converting enzyme (ACE) inhibitor (for example lisinopril) or a diuretic (for example furosemide or hydrochlorothiazide). It is to be understood that such a combination therapy constitutes a further aspect of the invention.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following non-limiting Examples in which, unless otherwise stated (i) concentrations and evaporations may be carried out by rotary evaporation in vacuo;

(ii) operations are carried out at room temperature, that is in the range 18°-26° C.;

(iii) flash column chromatography is performed on Merck Kieselgel 60 (Art. no. 9385) obtained from E Merck, Darmstadt, Germany;

(iv) yields, where given, are intended for the assistance of the reader only and are not necessarily the maximum attainable by diligent process development;

(v) $^1$H NMR spectra were determined at 200 MHz in CDCl$_3$ or d$_6$-dimethylsulphoxide using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; and (vi) the term "1H-tetrazol-5-yl" stands for "1H-1,2,3,4-tetrazol-5-yl".

EXAMPLE 1

1,1-Dimethylethyl 3-bromo-5-[[2-ethyl-5,6,7,8-tetrahydroquinolin-4-yloxy]methyl]-2-[2-(1H-tetrazol-5-yl)phenyl]-1H-indole-1-carboxylate (A) (100 mg) in a mixture of ethanol (15 ml) and 2M aqueous sodium hydroxide solution (5 ml) is heated at 60° C. for 3 hours. The mixture is cooled and acidified with 2M hydrochloric acid to pH 5 to 6. The mixture is then extracted with dichloromethane and the combined extracts are dried (MgSO$_4$) and evaporated to give 3-bromo-5-[[2-ethyl-5,6,7,8-tetrahydroquinolin-4-yloxy]methyl]-2-[2-(1H-tetrazol-5-yl)phenyl]-1H-indole.

The starting material A may be obtained as follows:

(i) Sodium hydride (60% dispersion in oil; 0.206 g) is added to a stirred solution of 2-ethyl-5,6,7,8-tetrahydro-4(1H)-quinolone (0.9 g) [itelf obtained as a solid (m.p. 226°-227° C.) using an analogous procedure to that described in Liebigs. Ann. Chem., 1982, 1656-1658 for the preparation of 2-methyl-5,6,7,8-tetrahydro-4(1H)-quinolone but starting from 2-ethyl-4(1H)-quinolone] in N,N-dimethylformamide (DMF) (25 ml). The mixture is stirred at 50° C. until evolution of hydrogen ceases and then 1,1-dimethylethyl 3-bromo-5-(bromomethyl)-2-[2-[2-(triphenylmethyl)-2H-tetrazol-5-yl]phenyl]-1H-indole-1-carboxylate (3.87 g) [obtained as described in European Patent Application, Publication No. 429257] is added. The solution is stirred at 50° C. for 30 minutes and then at ambient temperature for 72 hours. The solvent is removed by evaporation and the residue partitioned between ethyl acetate (50 ml) and water (50 ml). The organic layer is separated, washed with saturated sodium chloride solution (30 ml) and dried (MgSO$_4$). The solvent is removed by evaporation and the residue purified by flash chromatography, eluting with ethyl acetate/hexane (1:1 v/v with gradual increase in the proportion of ethyl acetate) to give 1,1-dimethylethyl 3-bromo-5-[[2-ethyl-5,6,7,8-tetrahydroquinolin-4-yloxy]methyl]-2-[2-[2-(triphenylmethyl)-2H-tetrazol-5-yl)phenyl]-1H-indole-1-carboxylate (B).

(ii) 6M Hydrochloric acid (2 ml) is added to a mixture of compound B (0.16 g) in methanol (20 ml) and the mixture is stirred for 16 hours. The mixture is adjusted to pH 5 to 6 with 2M sodium hydroxide solution, water (20 ml) is added and the mixture extracted with dichloromethane (3×20 ml). The combined extracts are dried (MgSO$_4$) and evaporated to give 1,1-dimethylethyl 3-bromo-5-[[2-ethyl-5,6,7,8-tetrahydroquinolin-4-yloxy]methyl]-2-[2-(1H-tetrazol-5-yl)phenyl]-1H-indole-1-carboxylate (A).

EXAMPLES 2-7

Using an analogous procedure to that described in Example 1, but starting from the appropriate compound of formula Q.H in part (i) in place of 2-ethyl-5,6,7,8-tetrahydro-4(1H)-quinolone, the following compounds of formula I may be obtained:

(Example 2): 3-bromo-5-[[2-ethylquinolin-4-yloxy]methyl]-2-[2-(1H-tetrazol-5-yl)phenyl]-1H-indole, starting from 2-ethyl-4(1H)-quinolone, itself obtained as described in EPA 412848.

(Example 3): 3-bromo-5-[[2,6-diethyl-3-iodopyrid-4-ylamino]methyl]-2-[2-(1H-tetrazol-5-yl)phenyl]-1H-indole, starting from 4-amino-2,6-diethyl-3-iodopyridine, itself obtained as follows:

(i) Methyl 4-amino-2,6-diethylpyridine-3-carboxylate (3.94 g), itself obtained using an analogous procedure to that described in Tet. Lett., 1990, 3485 but starting from 3-amino-2-pentenenitrile (obtained as described in J. Het. Chem., 1989, 26, 1575) and methyl propionylacetate, is added to a mixture of 2M sodium hydroxide solution (9.5 ml) and methanol (40 ml) and the mixture is heated at reflux for 16 hours. The solution is cooled to ambient temperature and volatile material is removed by evaporation. The residue is partitioned between ethyl acetate and a mixture of 2M hydrochloric acid (9.5 ml) and water (20 ml). The aqueous phase is separated, water is removed by evaporation and the residue is extracted with ethyl acetate/methanol (1:1 v/v). The combined organic extracts are filtered and solvent is removed from the filtrate by evaporation to give 4-amino-2,6-diethylpyridine-3-carboxylic acid (3.46 g) as a yellow-brown foam; NMR (d$_6$-DMSO): 1.18(m,6H), 2.64(q,2H), 3.12(q,2H), 6.49(s,1H), 8.28(broad s,2H),; mass spectrum (chemical ionisation, ammonia): 195(M+H)$^+$.

(ii) 4-Amino-2,6-diethylpyridine-3-carboxylic acid (3.26 g) is heated at 220° C. for 50 minutes. The residue is cooled to ambient temperature and purified by flash chromatography eluting with concentrated aqueous ammonia solution/dichloromethane/methanol (1:85:15 v/v) to give 4-amino-2,6-diethylpyridine (1.94 g) as a solid, m.p. 133°-137° C.; NMR (CDCl$_3$/d$_6$-DMSO): 1.24(t,6H), 2.68(q,4H), 4.48(broad s,2H), 6.27(s,2H); mass spectrum (chemical ionisation, ammonia): 151(M+H)$^+$.

(iii) 4-Amino-2,6-diethylpyridine (1.8 g) is added to a solution of iodine (3.1 g) and [bis(trifluoroacetoxy)iodo]benzene (5.7 g) in a mixture of dichloromethane (70 ml) and methanol (20 ml) and the mixture is stirred for 16 hours. Solvent is removed by evaporation and the residue is partitioned between ethyl acetate and a mixture of saturated sodium metabisulphite solution (50 ml) and saturated sodium carbonate solution (150 ml). The organic phase is separated, washed with saturated sodium chloride solution and dried. Solvent is removed by evaporation and the residue is purified by flash chromatography eluting with dichloromethane/methanol (97:3 v/v) to give 4-amino-2,6-diethyl-3-iodopyridine (1.33 g) as a solid, m.p. 72°-74° C.; NMR (CDCl$_3$): 1.25(m,6H), 2.65(q,2H), 2.96(q,2H), 4.59(broad s,2H), 6.30(s,1H); mass spectrum (chemical ionisation, ammonia): 277(M+H)$^+$.

(Example 4): 1-[[3-bromo-2-[2-(1H-tetrazol-5-yl)phenyl]-1H-indol-5-yl]methyl]-4-chloro-2,6-dimethyl-1H-pyrrolo[3,2-c]pyridine, starting from 4-chloro-2,6-dimethyl-1H-pyrrolo[3,2-c]pyridine (itself obtained using the method described in *Tetrahedron*, 1976, 32, 1383-1390).

(Example 5): 1-[[3-bromo-2-[2-(1H-tetrazol-5-yl)phenyl]-1H-indol-5yl]methyl]-5,7-dimethyl-1,6-naphthyrid-2(1H)-one, starting from 5,7-dimethyl-1,6-naphthyrid-2(1H)-one (itself obtained as described in *Chem. Pharm. Bull.* 1985, 33, 4764).

(Example 6): 3-[[3-bromo-2-[2-(1H-tetrazol-5-yl)phenyl]-1H-indol-5yl]methyl]-5,7-dimethyl-2-ethyl-3H-imidazo[4,5-b]pyridine, starting from 5,7-dimethyl-2-ethylimidazo[4,5-b]pyridine (itself obtained as described in European Patent Application, publication No. 400974).

(Example 7): 3-[[3-bromo-2-[2-(1H-tetrazol-5-yl)phenyl]-1H-indol-5-yl]methyl]-2-butyl-3H-imidazo[4,5-b]pyridine, starting from 2-butyl-3H-imidazo[4,5-b]pyridine (itself obtained as described in Indian J. Chem., Sec. B. 1978, 16B, 531).

EXAMPLE 8

Concentrated hydrochloric acid (1 ml) was added to a suspension of 4-[(3-bromo-2-(2-triphenylmethyl-2H-tetrazol-5-yl)phenyl)benzofuran-5-yl)methoxy]-2-ethyl-5,6,7,8-tetrahydroquinoline (A) (650 mg) in methanol (2 ml) and ethanol (4 ml). The mixture was warmed gently until the solid dissolved and then left to stand for 2 hours. The precipitated solid was filtered off, slurried with ether (10 ml) and recrystallised from methanol to give 4-[(3-bromo-2-(2-(1H-tetrazol-5-yl)phenyl)benzofuran-5-yl)methoxy]-2-ethyl-5,6,7,8-tetrahydroquinoline hydrochloride, m.p. 210°-212° C.; NMR (d$_6$-DMSO): 1.3(t, 3H), 1.65-1.9(m, 4H), 2.5-2.7(m, 2H), 2.9-3.1(m, 4H), 5.6(s, 2H), 7.55(s, 1H), 7.6(s, 2H), 7.7(s, 1H), 7.75-7.85(m, 2H), 7.9-8.0(m, H); mass spectrum (+ve fast atom bombardment (+FAB), DMSO/Methanol/nitrobenzyl alcohol(NBA)): 532 (M+H)$^+$; microanalysis, found: C, 57.0; H, 4.6; N, 12.4%; C$_{27}$H$_{24}$BrN$_5$O$_2$.HCl requires: C, 57.2; H, 4.45; N, 12.4%.

The starting material (A) was obtained as a foam in 51% yield using an analogous procedure to that described in Example 1, part (i), but starting from 5-[2-(3-bromo-5-(bromomethyl)-benzofuran-2-yl)phenyl]-triphenylmethyl-2H-tetrazole (obtained as described in European Patent Application, Publication No. 434249); NMR: 1.3(t, 3H), 1.7-1.95(m, 4H), 2.7(t, 2H), 2.75(q, 2H), 2.9(t, 2H), 5.2(s, 2H), 6.6(s, 1H), 6.8-6.9(m, 6H), 7.05-7.4(m, 11H), 7.45-7.8(m, 4H), 8.2(dd, 1H).

EXAMPLE 9

Using an analogous procedure to that described in Example 8, but starting from 1-[(3-bromo-2-(2-(2-triphenylmethyl-2H-tetrazol-5-yl)phenyl)benzofuran-5-yl)methyl]-5,7-diethyl-1,6-naphthyridin-2(1H)-one (A), there was obtained in 33% yield 1-[(3-bromo-2-(2-(1H-tetrazol-5-yl)phenyl)benzofuran-5-yl)methyl]-5,7-diethyl-1,6-naphthyridin-2(1H)-one hydrochloride, m.p. 214°-216° C.; NMR (d$_6$-DMSO): 1.25-1.35(2×t, 6H), 3.0(q, 2H), 3.3(q, 2H), 5.7(s, 2H), 7.0(d, 1H), 7.4(d, 1H), 7.5(d, 1H), 7.6(s, 1H), 7.7-8.0 (m, 5H), 8.4(d, 1H); mass spectrum (+ve FAB, methanol/NBA): 555 (M+H)$^+$; microanalysis, found: C, 56.3; H, 4.4; N, 13.7; H$_2$O, 1.2%; C$_{28}$H$_{23}$BrN$_6$O$_2$.HCl.0.5H$_2$O.0.1.Et$_2$O requires: C, 56.1; H, 4.3; N, 13.8; H$_2$O, 1.5%.

The starting material A was obtained as follows:

(i) Palladium (II) acetate (50 mg) and tri(2-methylphenyl)-phosphine (50 mg) were added to a solution of 4-amino-2,6-diethyl-3-iodopyridine (1.3 g), ethyl acrylate (1.2 ml) and triethylamine (1.2 ml) in DMF (25 ml). The mixture was heated at 130° C. for 2 hours and then allowed to cool. Volatile material was removed by evaporation and the residue was purified by flash chromatography, eluting with aqueous ammonia (density 0.88 g/ml)/dichloromethane/methanol (1:200:20, v/v/v) to give ethyl-3-[(4-amino-2,6-diethyl)pyridin-3-yl]acrylate as an oil; NMR (CDCl$_3$): 1.15-1.45(m, 9H), 2.7(g, 2H), 2.8(q, 2H), 4.25(q, 2H), 4.5(broad s, 2H), 6.25(d, 2H), 7.75(d, 2H); mass spectrum (chemical ionisation, ammonia): 249 (M+H)$^+$.

(ii) A solution of ethyl-3-[(4-amino-2,6-diethyl)pyridin-3-yl]acrylate (600 mg) in dry methanol (10 ml) was added to a solution of sodium methoxide, prepared from sodium (500 mg) and dry methanol (30 ml), and the mixture was heated at reflux under an atmosphere of argon for 3 hours. Solvent was removed by evaporation and the residue partitioned between ethyl acetate and water. The aqueous phase was separated and extracted with ethyl acetate. The combined organic solutions were washed with saturated sodium chloride solution and then dried (MgSO$_4$). The solvent was removed by evaporation and the residue was triturated with ether to give 5,7-diethyl-1,6-naphthyridin-2(1H)-one (310 mg), as a solid, m.p. 170°–171° C.; NMR (CDCl$_3$): 1.45(m, 6H), 2.85(q, 2H), 3.1(q, 2H), 6.7(d, 1H), 6.95(s, 1H), 8.05(d, 1H), 12.05(broad s, 1H): mass spectrum (chemical ionisation, ammonia): 203(M+H)+.

(iii) A mixture of 5,7-diethyl-1,6-naphthyridin-2(1H)-one (291 mg), 5-[2-(3-bromo-5-(bromomethyl)-benzofuran-2-yl)phenyl]-2-triphenylmethyl-2H-tetrazole (1.30 g), potassium t-butoxide (168 mg) and 1,4,7,10,13,16-hexaoxacyclooctadecane (40 mg) in dry tetrahydrofuran (15 ml) was stirred under an atmosphere of argon for 18 hours. Saturated sodium chloride solution (25 ml) was added and the mixture was extracted with ether (2×25 ml). The extracts were dried (MgSO$_4$) and concentrated by evaporation. The residue was purified by flash chromatography, eluting with ethyl acetate/hexane (3:1 v/v), to give 1-[(3-bromo-2-(2-(2-triphenylmethyl-2H-tetrazol-5-yl)phenyl)benzofuran-5-yl)methyl]-5,7-diethyl-1,6-naphthyridin-2(1H)-one (A) (640 mg) as a foam; NMR: 1.2(t, 3H), 1.35(t, 3H), 2.7(q, 2H), 3.1(q, 2H), 5.6(s, 2H), 6.8–7.25(m, 19H), 7.35(s, 1H), 7.5–7.7(m, 3H), 8.0(d, 1H), 8.2(d, 1H).

EXAMPLE 10

Using an analogous procedure to that described in Example 8, but starting from 1-[(3-bromo-2-(2-(2-triphenylmethyl-2H-tetrazol-5-yl)phenyl)benzofuran-5-yl)methyl]-5,7-diethyl-1,2,3,4-tetrahydro-1,6-naphthyridin-2-one (A), there may be obtained 1-[(3-bromo-2-(2-(1H-tetrazol-5-yl)phenyl)benzofuran-5-yl)methyl]-5,7-diethyl-1,2,3,4-tetrahydro-1,6-naphthyridin-2-one hydrochloride.

The starting material A may be obtained using an analogous procedure to that described in Example 9, part (iii), but starting from 5,7-diethyl-1,2,3,4-tetrahydro-1,6-naphthyridin-2-one, itself obtained as follows:

A solution of ethyl-3-[(4-amino-2,6-diethyl)pyridin-3-yl]-acrylate (540 mg) in ethanol (30 ml) was catalytically hydrogenated over 30% palladium on carbon. When uptake of hydrogen ceased the catalyst was removed by filtration through diatomaceous earth. The filtrate was concentrated by evaporation and the residue was purified by flash chromatography, eluting with dichloromethane/methanol (9:1 v/v), to give 5,7-diethyl-1,2,3,4-tetrahydro-1,6-naphthyridin-2-one (380 mg) as a solid, m.p. 100° C.; NMR (CDCl$_3$): 1.15–1.4(m,6H), 2.6–2.9(m,6H), 2.95(t,2H), 6.45(s,1H), 8.5(broad s,1H); mass spectrum (chemical ionisation, ammonia): 205(M+H)+.

EXAMPLES 11–15

Using an analogous procedure to that described in Example 8, but starting from the appropriate compound of formula IV, which itself may be obtained using an analogous procedure to that described in Example 1, part (i) or Example 9, part (iii) but starting from the appropriate compound of formula Q.H indicated and 5-[2-(3-bromo-5-(bromomethyl)benzofuran-2-yl)phenyl]-2-triphenylmethyl-2H-tetrazole, the following compounds of formula I may be obtained:

(Example 11): 4-[(3-bromo-2-(2-(1H-tetrazol-5-yl)phenyl)benzofuran-5-yl)methoxy]2-ethylquinoline hydrochloride, starting from Q.H=2-ethyl-4(1H)-quinolone, itself obtained as described in EPA 412848.

(Example 12): 4-[(3-bromo-2-(2-(1H-tetrazol-5-yl)phenyl)benzofuran-5-yl)methylamino]-2,6-diethyl-3-iodopyridine hydrochloride, starting from Q.H=4-amino-2,6-diethylpyridine.

(Example 13): 1-[[3-bromo-2-[2-(1H-tetrazol-5-yl)phenyl]-benzofuran-5-yl]methyl]-4-chloro-2,6-dimethyl-1H-pyrrolo[3,2-c]pyridine hydrochloride, starting from Q.H=4-chloro-2,6-dimethyl-1H-pyrrolo[3,2-c]pyridine.

(Example 14): 3-[[3-bromo-2-[2-(1H-tetrazol-5-yl)phenyl]-benzofuran-5-yl]methyl]-5,7-dimethyl-2-ethyl-3H-imidazo[4,5-b]pyridine hydrochloride, starting from Q.H=5,7-dimethyl-2-ethyl-3H-imidazo[4,5-b]pyridine.

(Example 15): 3-[[3-bromo-2-[2-(1H-tetrazol-5-yl)phenyl]-benzofuran-5-yl]methyl]-2-butyl-3H-imidazo[4,5-b]pyridine hydrochloride, starting from Q.H=2-butyl-3H-imidazo[4,5-b]pyridine.

EXAMPLE 16

(Note: all parts by weight)

The compounds of the invention may be administered for therapeutic or prophylactic use to warm-blooded animals such as man in the form of conventional pharmaceutical compositions, typical examples

| a) Capsule (for oral administration) | |
|---|---|
| Active ingredient * | 20 |
| Lactose powder | 578.5 |
| Magnesium stearate | 1.5 |
| b) Tablet (for oral administration) | |
| Active ingredient * | 50 |
| Microcrystalline cellulose | 400 |
| Starch (regelatinised) | 47.5 |
| Magnesium stearate | 2.5 |
| c) Injectable Solution (for intravenous administration) | |
| Active ingredient * | 0.05–1.0 |
| Propylene glycol | 5.0 |
| Polyethylene glycol (300) | 3.0–5.0 |
| Purified water | to 100% |
| d) Injectable Suspension (for Intramuscular administration) | |
| Active ingredient * | 0.05–1.0 |
| Methylcellulose | 0.5 |
| Tween 80 | 0.05 |
| Benzyl alcohol | 0.9 |
| Benzalkonium chloride | 0.1 |
| Purified water | to 100% |

Note: the active ingredient * may typically be an Example described hereinbefore and will conveniently be present as a pharmaceutically acceptable acid-addition salt, such as the hydrochloride salt. Tablets and capsules formulations may be coated in conventional manner in order to modify or sustain dissolution of the active ingredient. Thus, for example, they may be coated with a conventional enterically digestible coating.

Chemical Formulae

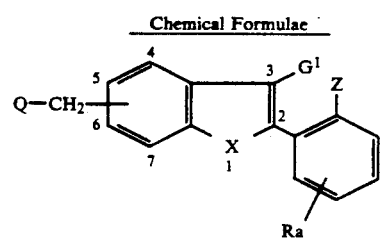

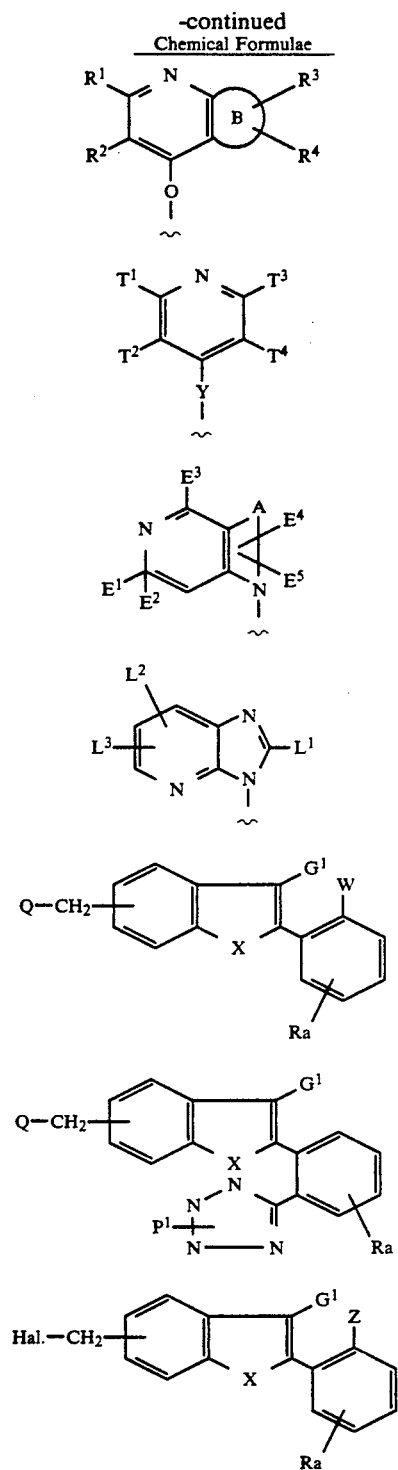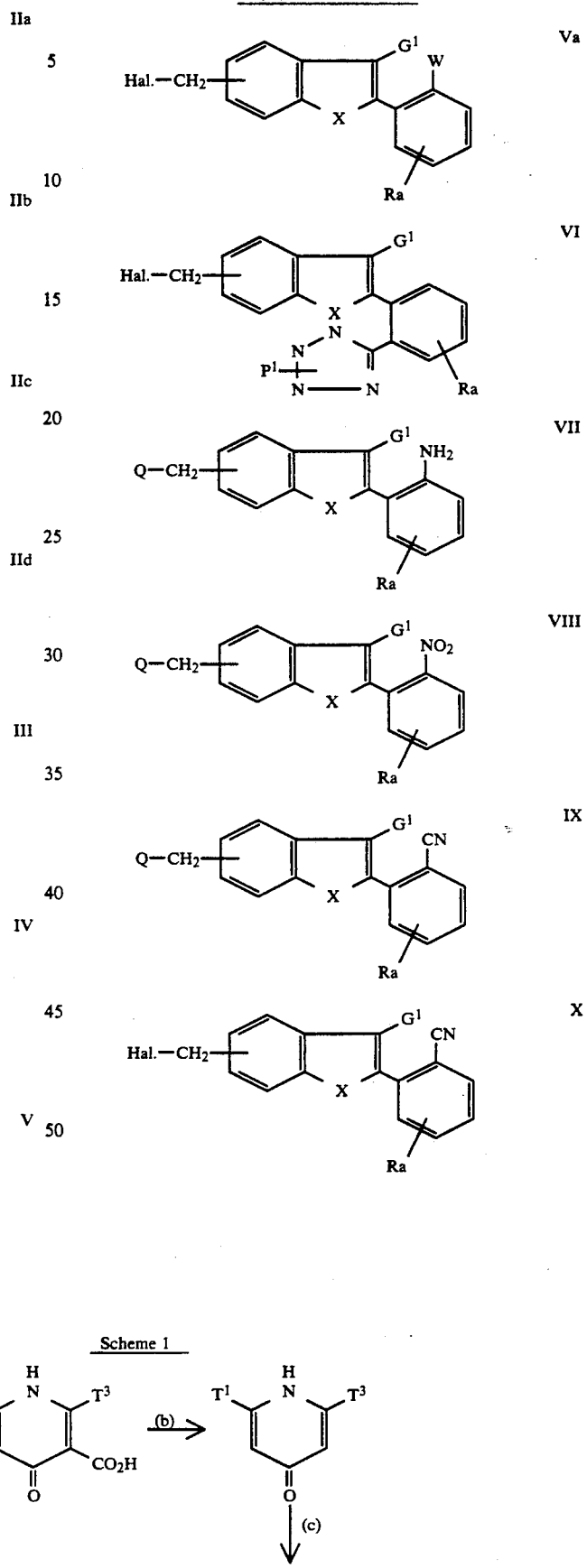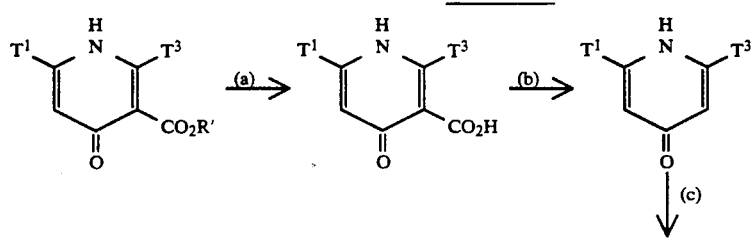

-continued
Scheme 1

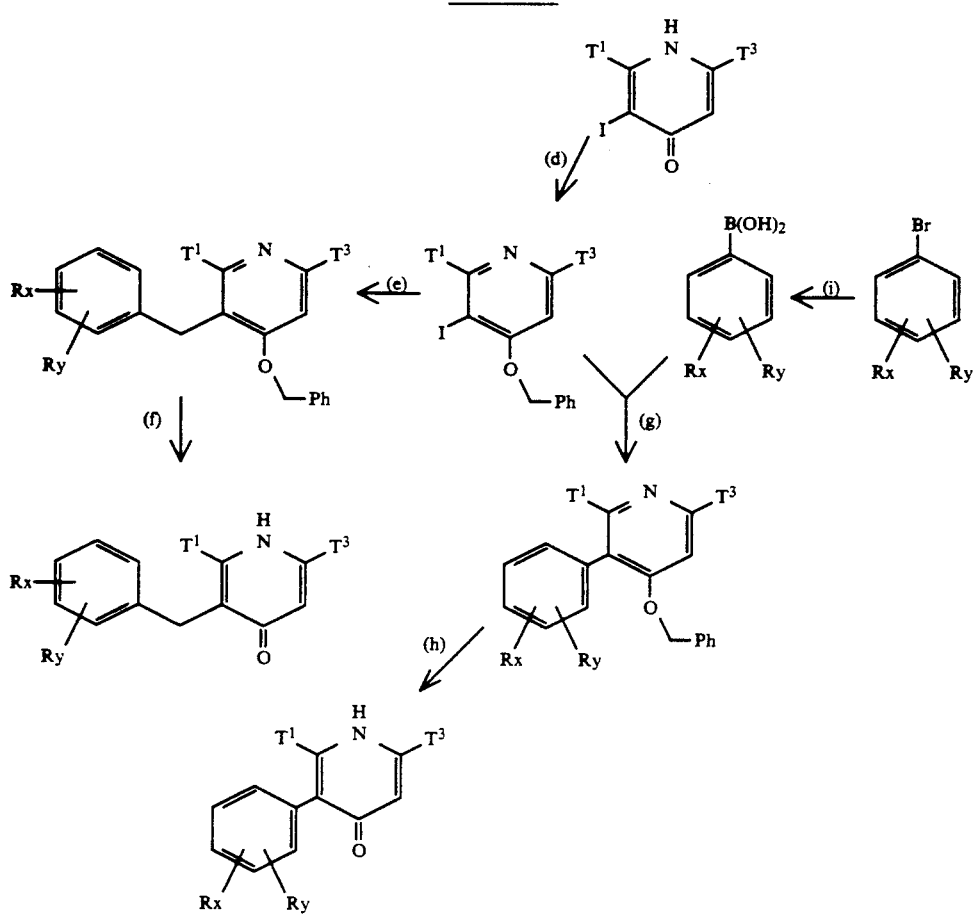

Note:
$T^1 = T^3 =$ methyl or ethyl; Rx and Ry are optional substituents; Ph = phenyl; R' = lower alkyl Reagents:
(a) NaOH, methanol, water, reflux
(b) Sublimation at 250° C.
(c) Iodine, NaOH, water
(d) $C_6H_5CH_2Cl$, NaH, DMF, 50° C.
(e) Product from (d) added to (Rx)(Ry)PhCH$_2$ZnBr in THF (from activated zinc, (Rx)(Ry)PhCH$_2$Br in THF), then $(Ph_3P)_4Pd$
(f) hydrogenation over palladium on carbon, methanol
(g) $(Ph_3P)_4Pd$, methanol, aq. NaHCO$_3$, toluene, reflux
(h) ammonium formate, 10% palladium on carbon, methanol
(i) tert-ButylLi/pentane; trimethyl borate/THF/−78° C.; aq. HCl Scheme 2

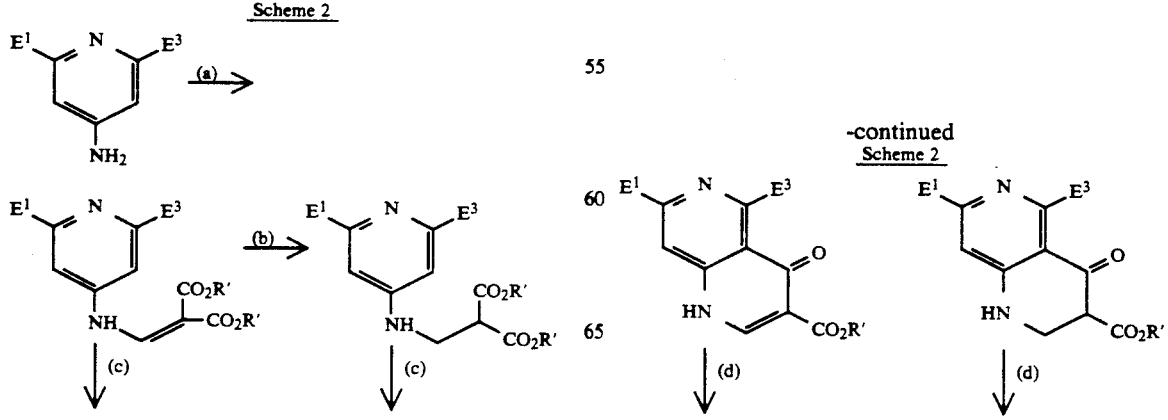

-continued
Scheme 2

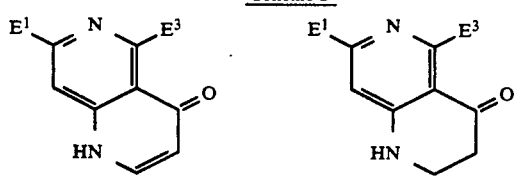

Note:
R' = lower alkyl
Reagents:
(a) R'OCH=C(CO$_2$R')$_2$, 110° C.
(b) hydrogen, Pd on C or PtO$_2$
(c) Ph—Ph/Ph—O—Ph mixture, reflux
(d) (i) NaOH; (ii) as for step (c)

Scheme 3

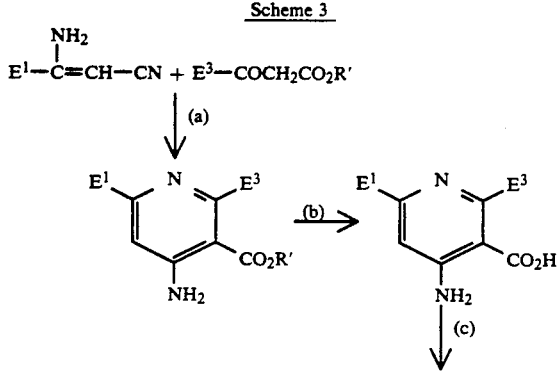

-continued
Scheme 3

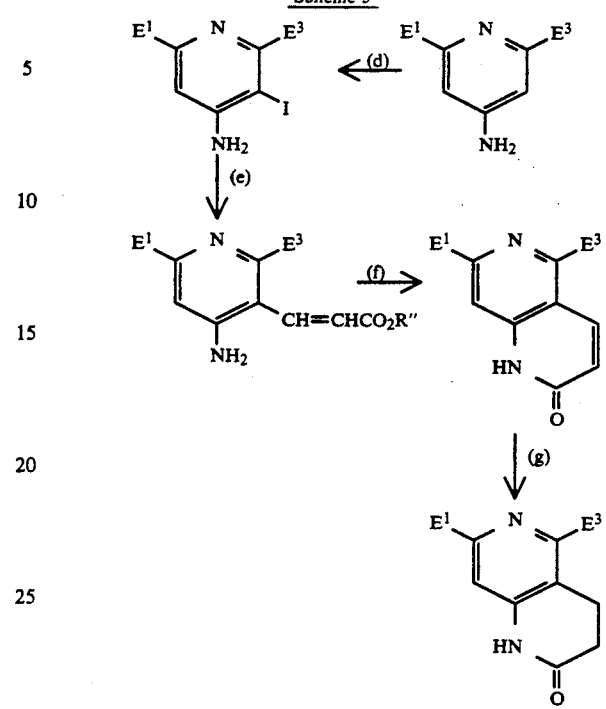

Note:
R' = lower alkyl; R'' = lower alkyl.
Reagents:
(a) SnCl$_4$, toluene, reflux
(b) aqu. NaOH, methanol, reflux; then HCl
(c) heat, 220° C.
(d) I$_2$, [bis(trifluoroacetoxy)iodo]benzene, CH$_2$Cl$_2$, methanol
(e) Pd(II)acetate, tri(2-methylphenyl)phosphine, Et$_3$N, DMF, 130° C., CH$_2$=CHCO$_2$R''
(f) NaOCH$_3$, methanol, reflux
(g) hydrogen, palladium on carbon, acetic acid/ethanol, 20 atmospheres, 70° C.

Scheme 4

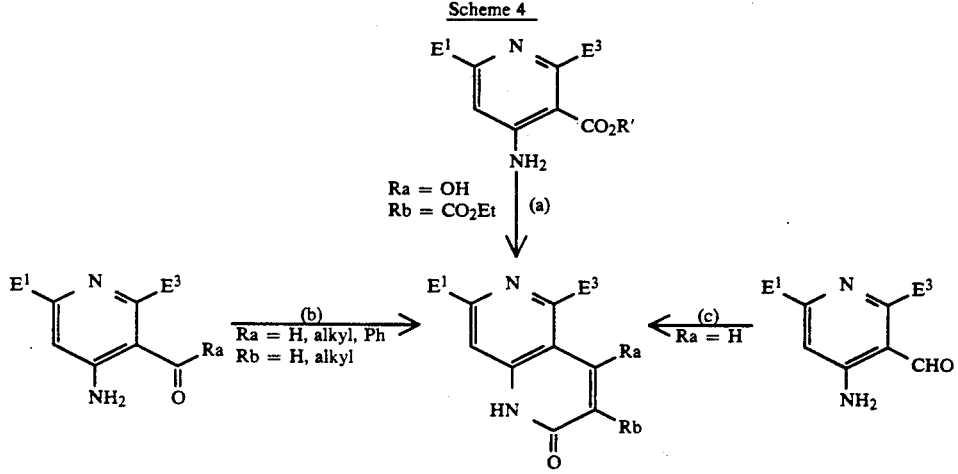

Scheme 4
-continued

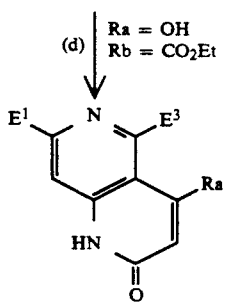

Note:
Et = ethyl; Ph = phenyl; R' = lower alkyl
Reagents:
(a) diethyl malonate, NaOEt, EtOH, 150° C., autoclave
(b) $Ph_3P=C(Rb)CO_2Et$, xylene or toluene, reflux
(c) $RbCH_2CO_2Et$ (e.g. Rb = $CO_2Et$, Ph, Pyridyl, CN, SPh), EtOH, piperidine, reflux
(d) aqu. HCl, dioxan, reflux

Scheme 5

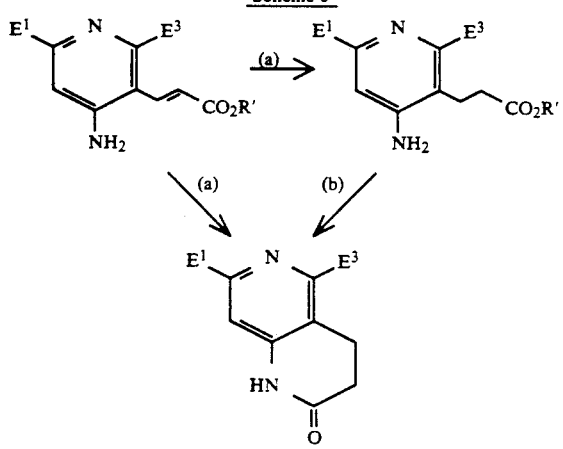

Note:
R' = lower alkyl
Reagents:
(a) hydrogen, Pd on C or $PtO_2$
(b) heat

Scheme 7

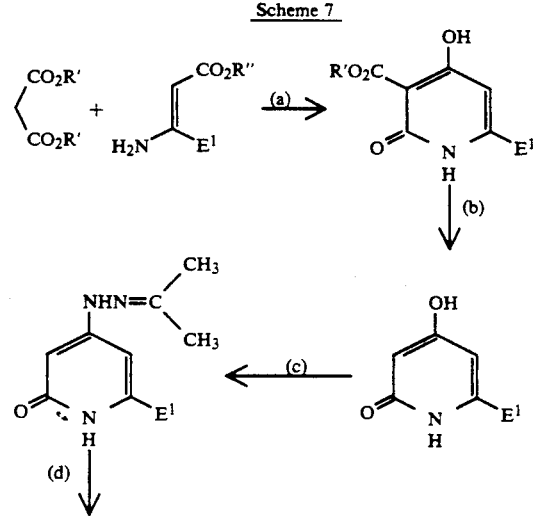

Scheme 6

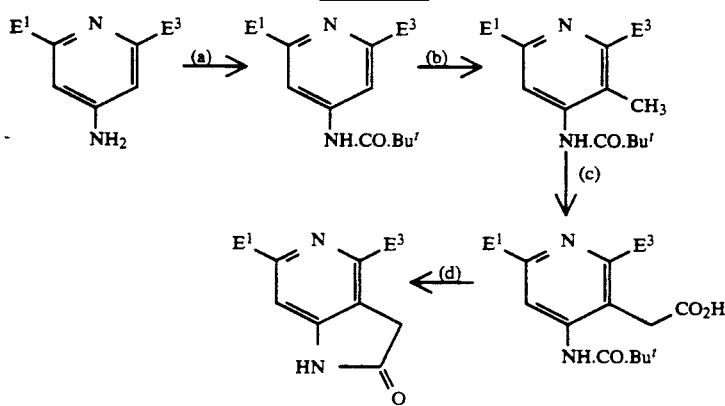

Reagents:
(a) 1-(tert-butyl.CO)imidazole, toluene, heat
(b) (i) tert-butyllithium (2 equivalents), −78° C., THF; (ii) iodomethane
(c) as (b)(i); then carbon dioxide
(d) aqueous HCl, heat -continued
Scheme 7

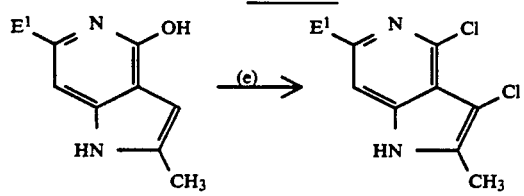

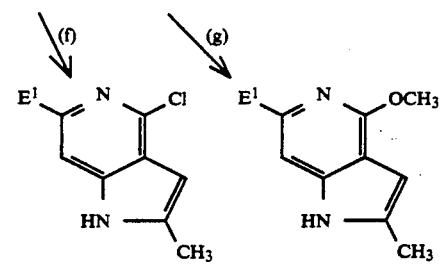

Note:
R' and R'' = lower alkyl;
Reagents:
(a) NaOMe, heat
(b) (i) NaOH (ii) HCl (iii) heat
(c) hydrazine hydrate, 2-ethoxyethanol, reflux; then acetone, reflux
(d) Ph—Ph/Ph—O—Ph mixture, reflux
(e) POCl₃, PCl₅, heat
(f) POCl₃ (freshly distilled), reflux
(g) (CH₃)₃OBF₄, dichloromethane

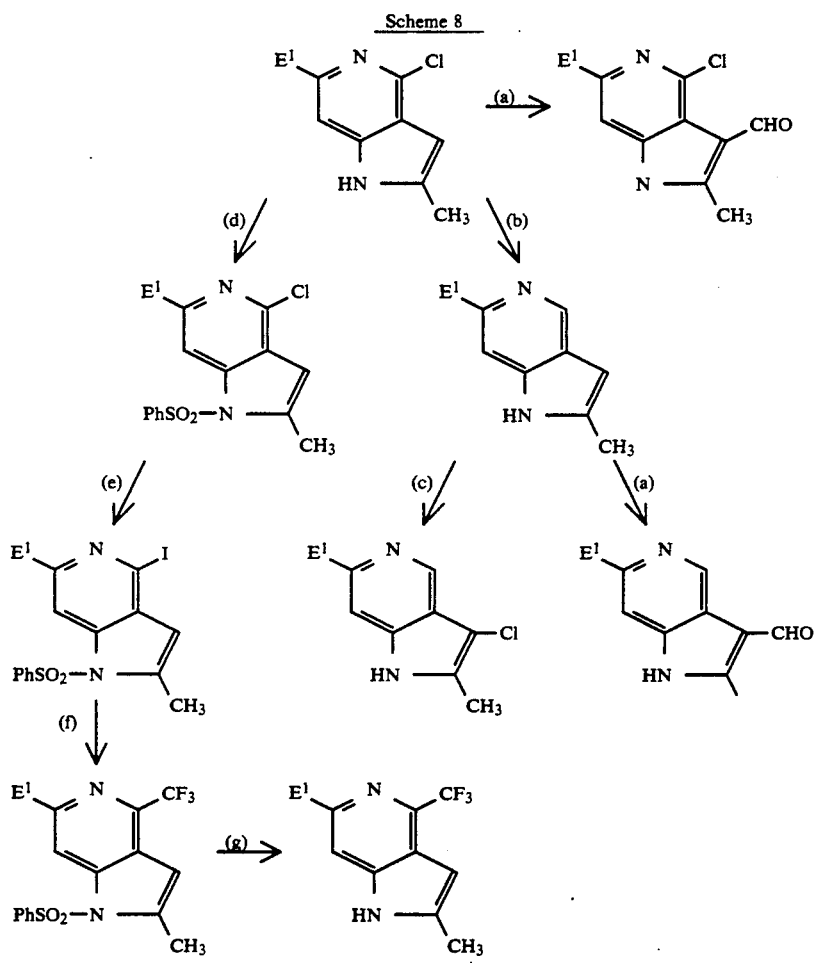

Note:
Ph = phenyl
Reagents:
(a) POCl₃/DMF
(b) Catalytic hydrogenation over palladium on carbon
(c) N-Chlorosuccinimide, dichloromethane
(d) (i) n-BuLi, THF/hexane, −78 to 0° C. (ii) PhSO₂Cl, THF, −78 to ambient
(e) NaI, aqueous HI, methyl ethyl ketone, reflux
(f) CuI, KF, triethyl(trifluoromethyl)silane, DMF/NMP, 80° C.
(g) NaOH, aqu. methanol, reflux Scheme 9
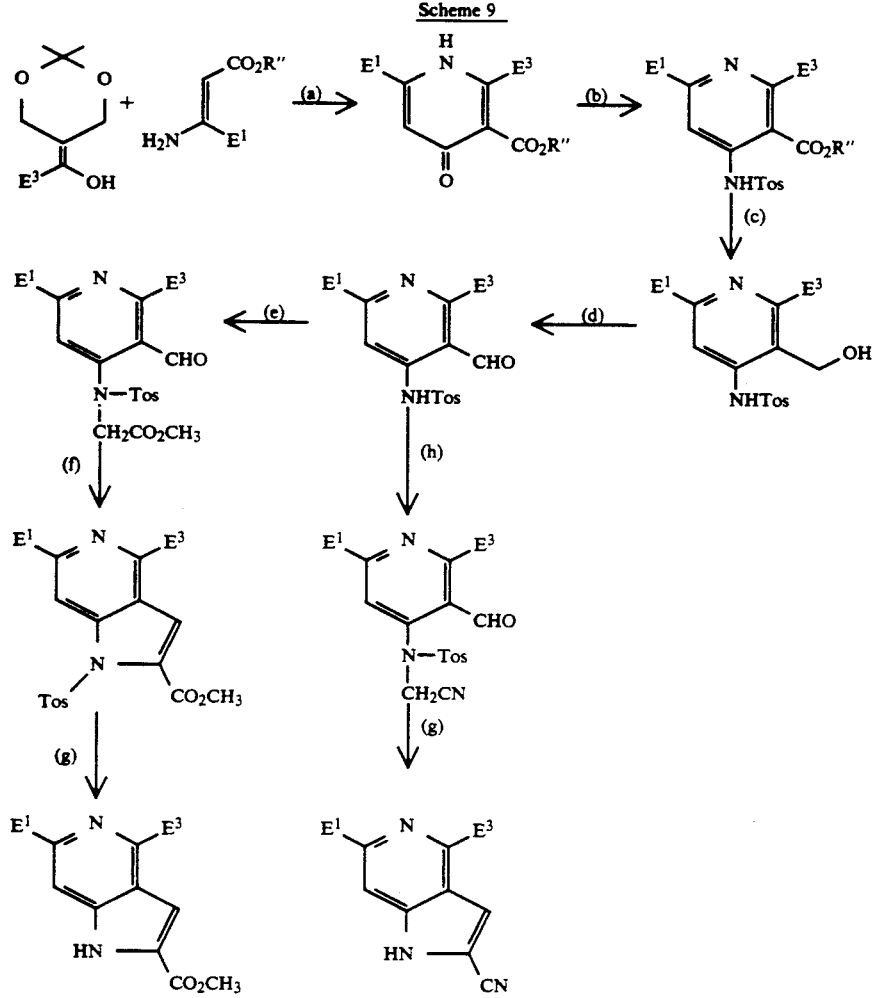
Note:
R'' = lower alkyl; Tos = p-toluenesulphonyl (tosyl)
Reagents:
(a) Heat, 120° C.
(b) p-Toluenesulphonyl isocyanate, acetonitrile, reflux
(c) Lithium aluminium hydride, THF, reflux
(d) Activated MnO₂, toluene, reflux
(e) NaH, DMF, BrCH₂CO₂CH₃, 0° C.
(f) (i) NaN(SiMe₃)₂, THF, 0° C.; (ii) Pyridine, SOCl₂, 0° C.
(g) NaN(SiMe₃)₂, THF
(h) NaH, DMF, BrCH₂CN, 0° C.
Scheme 10
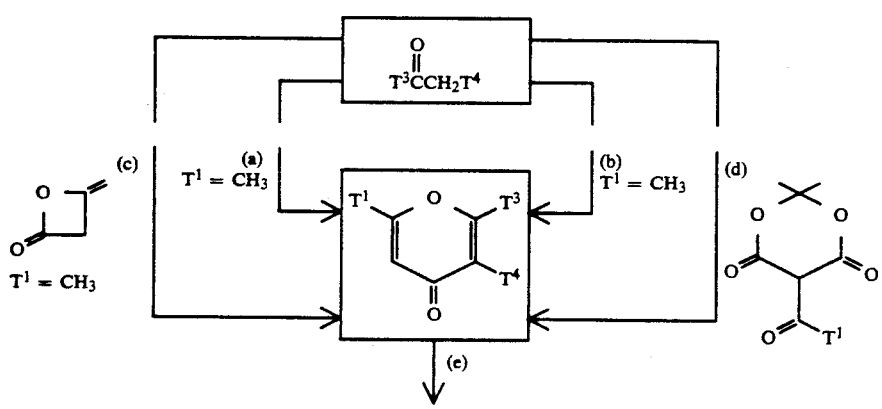

Scheme 10

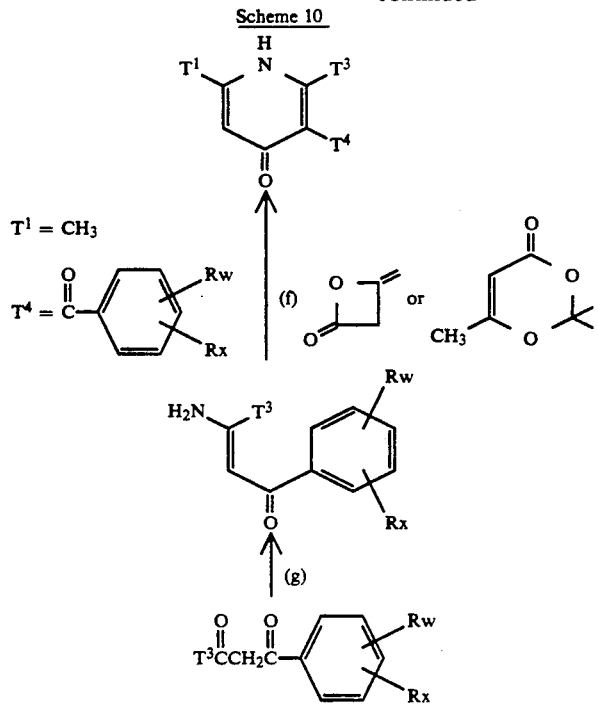

$T^1 = CH_3$ $T^4 = $ 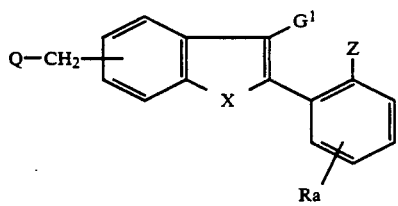

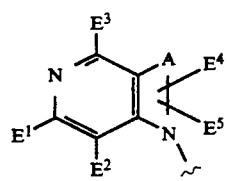

Note:
Rw and Rx are optional substituents
Reagents:
(a) polyphosphoric acid, acetic acid
(b) (i) boron trifluoride, acetic anhydride (ii) NaH or (isopropyl)$_2$NLi, ethyl acetate (iii) benzene, PTSA, heat or conc. H$_2$SO$_4$, ambient temp.
(c) acetic acid, 0–50° C.
(d) heat, 120° C.
(e) ethanolic ammonia, 120° C., sealed tube
(f) heat
(g) ethanolic ammonia

What we claim is:
1. A heterocyclic compound of the formula I wherein Q is a group of the partial structural formula IIc, in which linking group A of formula IIc is selected from —CH=CH—, —CH=CH—CO—, —CO—CH=CH—, —CO—CH$_2$—CH$_2$—, —CH$_2$—CH$_2$—CO, —CH$_2$—CO and —CO—CH$_2$;

$E^1$ is hydrogen, (1-8C)alkyl or trifluoromethyl;
$E^2$ is hydrogen, (1-8C)alkyl, halogeno, (1-4C)alkoxy, trifluoromethyl, carboxy, (1-4C)alkoxycarbonyl, (3-6C)alkenyloxycarbonyl, cyano, nitro, (1-4C)alkanoyl, (1-4C)alkyl.S(O)$_m$—(in which m is zero, 1 or 2) or phenylsulphonyl;

$E^3$ is hydrogen, (1-8C)alkyl, (1-4C)alkoxy, halogeno or trifluoromethyl;

$E^4$ and $E^5$ are optional substituents on linking group A independently selected from (1-4C)alkyl, substituted (1-4C)alkyl having one or more fluoro substituents, phenyl, pyridyl, alkoxy, halogeno, cyano, nitro, carboxy, (1-4C)alkoxycarbonyl, (3-6C)alkenyloxycarbonyl; carbamoyl, N-alkylcarbamoyl and di-(N-alkyl)carbamoyl of up to 7 carbon atoms, (1-4C)alkylthio, (1-4C)alkylsulphinyl, (1-4C)alkylsulphonyl, phenylthio, phenylsulphinyl, phenylsulphonyl and (1-4c)alkanoyl;

$G^1$ is selected from hydrogen, (1-4C)alkyl optionally bearing one or more fluoro substituents, halogeno, cyano, (1-4C)alkoxycarbonyl, (1-4C)alkanoyl, carbamoyl, N-alkylcarbamoyl and di-(N-alkyl)carbamoyl of up to 7 carbon atoms;

X is oxygen, sulphur or a group of the formula —NRc wherein Rc is hydrogen or (1-4C)alkyl;

Ra is selected from hydrogen, (1-4C)alkyl, (1-4C)alkoxy, halogeno, trifluoromethyl, cyano and nitro;

Z is 1H-tetrazol-5-yl, carboxy or a group of the formula CF$_3$SO$_2$NH—; and wherein any of said phenyl moieties of $E^2$ may be substituted or bear one or two substituents independently selected from (1-4C)alkyl, (1-4C)alkoxy, halogeno, cyano and trifluoromethyl; or a non-toxic salt thereof.

2. A compound as claimed in claim 1 but excluding those compounds wherein one or both of $E^4$ and $E^5$ is selected from phenyl, pyridyl, carbamoyl, N-alkylcarbamoyl and di-(N-alkyl)carbamoyl of up to 7 carbon atoms, (1-4C)alkylthio, (1-4C)alkylsulphinyl, (1-4C)alkylsulphonyl, phenylthio, phenylsulphinyl and phenylsulphonyl; or a non-toxic salt thereof.

3. A compound as claimed in claim 1 wherein $E^1$ is hydrogen, methyl, ethyl, propyl, butyl, isobutyl, sec-butyl, pentyl, hexyl or trifluoromethyl;

$E^2$ is hydrogen, methyl, ethyl, propyl, butyl, isobutyl, sec-butyl, pentyl, hexyl, fluoro, chloro, bromo, iodo, methoxy, ethoxy, propoxy, trifluoromethyl, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, cyano, nitro, formyl, acetyl, butyryl, methylthio, ethylthio, methylsulphinyl, ethylsulphinyl, methylsulphonyl, ethylsulphonyl or phenylsulphonyl;

$E^3$ is hydrogen, methyl, ethyl, propyl, butyl, isobutyl, sec-butyl, pentyl, hexyl, fluoro, chloro, bromo, iodo, methoxy, ethyoxy, propoxy or trifluoromethyl;

$E^4$ and $E^5$ are optional substituents on linking group A independently selected from methyl, ethyl, fluoromethyl, trifluoromethyl, 2,2,2-trifluoroethyl, pentafluoroethyl, phenyl, pyridyl, methoxy, ethoxy, chloro, bromo, iodo, cyano, nitro, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, carbamoyl, N-methylcarbamoyl, N-ethylcarbamoyl, N,N-dimethylcarbamoyl, N,N-diethylcarbamoyl, methylthio, ethylthio, methylsulphinyl, ethylsulphinyl, methylsulphonyl, ethylsulphonyl or phenylthio, phenylsulphinyl; phenylsulphonyl, formyl, acetyl and butyryl;

$G^1$ is selected from hydrogen, methyl, ethyl, propyl, fluoromethyl, trifluoromethyl, 2,2,2-trifluoroethyl, pentafluoroethyl, chloro, bromo, iodo, cyano, methoxycarbonyl, ethoxycarbonyl, formyl, acetyl, butyryl, carbamoyl, N-methylcarbamoyl, N-ethylcarbamoyl, N,N-dimethylcarbamoyl, and N,N-diethylcarbamoyl;

X is oxygen, sulphur or a group of the formula -NRc wherein Rc is hydrogen, methyl or ethyl;

Ra is selected from hydrogen, methyl, ethyl, methoxy, ethoxy, chloro, bromo, iodo, trifluoromethyl, cyano and nitro; and wherein any of said phenyl moieties of $E^2$ may be unsubstituted or bear one or two substituents independently selected from methyl, ethyl, methoxy, ethoxy, chloro, bromo, iodo, cyano and trifluoromethyl; or a non-toxic salt thereof.

4. A compound of formula I as claimed in claim 1, wherein Q is selected from 2,6-di-(1-4C)alkyl-4-halogeno-1$\underline{H}$-pyrrolo(3,2-c)pyrid-1-yl, 5,7-di-(1-4C)alkyl-2-oxo-1,2-dihydro-1,6-naphthyridin-1-yl, and 5,7-di-(1-4C)alkyl-2-oxo-1,2,3,4-tetrahydro-1,6-naphthyridin-1-yl.

5. A compound of the formula I as claimed in claim 1 or claim 4 wherein X is oxygen.

6. A compound of the formula I which is 1-(3-bromo-2-(2-(1H-tetrazol-5-yl)phenyl)benzofuran-5-yl)methyl)-5,7-diethyl-1,6-naphthyridin-2(1$\underline{H}$)-one; or a non-toxic salt thereof.

7. A salt as claimed in claim 1 which is selected from salts with acids forming physiologically acceptable anions and salts with bases forming physiologically acceptable cations.

8. A pharmaceutical composition which comprises a compound of the formula I, or a non-toxic salt thereof, as claimed in claim 1, together with a pharmaceutically acceptable diluent or carrier.

9. A method for antagonising one or more of the actions of angiotensin II in a warm-blooded animal requiring such treatment which comprises administering to said animal an antagonistically effective amount of a compound of formula I, or a non-toxic salt thereof, as defined in claim 1.

* * * * *